(12) United States Patent
Min et al.

(10) Patent No.: US 9,277,968 B2
(45) Date of Patent: Mar. 8, 2016

(54) MEDICAL ROBOT SYSTEM AND METHOD FOR CONTROLLING THE SAME

(71) Applicant: SAMSUNG ELECTRONICS CO., LTD., Suwon-si (KR)

(72) Inventors: Seung Ki Min, Suwon-si (KR); Woong Kwon, Seongnam-si (KR)

(73) Assignee: SAMSUNG ELECTRONICS CO., LTD., Gyeonggi-Do (KR)

( * ) Notice: Subject to any disclaimer, the term of this patent is extended or adjusted under 35 U.S.C. 154(b) by 201 days.

(21) Appl. No.: 13/707,826

(22) Filed: Dec. 7, 2012

(65) Prior Publication Data

US 2013/0150865 A1    Jun. 13, 2013

(30) Foreign Application Priority Data

Dec. 9, 2011   (KR) .................. 10-2011-0131935

(51) Int. Cl.
*A61B 19/00*   (2006.01)
*A61B 17/34*   (2006.01)
*A61B 17/00*   (2006.01)

(52) U.S. Cl.
CPC .......... *A61B 19/201* (2013.01); *A61B 17/3421* (2013.01); *A61B 19/2203* (2013.01); *A61B 19/5244* (2013.01); *A61B 19/56* (2013.01); *A61B 2017/00119* (2013.01); *A61B 2019/464* (2013.01); *A61B 2019/4857* (2013.01)

(58) Field of Classification Search
CPC .... A61B 19/2203; A61B 19/26; A61B 19/22; A61B 17/29; A61B 2017/00477; A61B 2017/3445; A61B 2019/2211; A61B 2019/223; A61B 2019/2234; A61B 2019/2242; A61B 2019/265; A61B 2019/4868; A61B 2019/464; A61B 5/064; A61B 19/52; A61B 19/5244; A61B 1/04; A61B 1/317; A61B 19/56; A61B 2019/505; A61B 2019/508; A61B 2019/5231; A61B 2019/5238; A61B 2019/5255; A61B 2019/5268; A61B 2019/5483; A61B 17/3403; A61B 2019/562; A61B 19/30; A61B 2017/00115; A61B 2017/00119; A61B 2017/3405; A61B 2019/2223; A61B 2019/2269; A61B 2019/2292; A61B 2019/2296; A61B 2019/301; A61B 2019/461; A61B 2019/4894; A61B 2019/507; A61B 2019/5229; A61B 2019/5259; A61B 2019/5272; A61B 2019/5291; A61B 19/20; A61B 18/1477; A61B 19/201; A61B 2019/5276; A61B 2018/1425; A61B 19/5212; A61B 2017/00725; A61B 17/3423; A61B 17/3462; A61B 2019/465; A61B 2017/3427; A61B 2017/3492; A61B 2017/00862; A61B 2019/4857; A61B 17/3421; B25J 3/04; B25J 15/04; B25J 18/04; G09B 23/28; G09B 19/24

See application file for complete search history.

(56) References Cited

U.S. PATENT DOCUMENTS 5,575,798 A * 11/1996 Koutrouvelis ................ 606/130
5,976,156 A * 11/1999 Taylor et al. .................. 606/130

(Continued)

FOREIGN PATENT DOCUMENTS

KR    10-0778387    11/2007

*Primary Examiner* — Bao Long T Nguyen
(74) *Attorney, Agent, or Firm* — Harness, Dickey & Pierce, P.L.C.

(57) ABSTRACT

A medical robot system and a method for controlling the same. The medical robot system includes a trocar, inserted into an incision of a patient, to guide a surgical apparatus and transmit at least one of position information of the surgical apparatus and pressure information of the surgical apparatus, and a console to display a screen including at least one of the position information and the pressure information.

18 Claims, 7 Drawing Sheets

(56) References Cited

U.S. PATENT DOCUMENTS

| | | | |
|---|---|---|---|
| 6,484,049 B1* | 11/2002 | Seeley et al. | 600/426 |
| 6,620,174 B2* | 9/2003 | Jensen et al. | 606/130 |
| 7,297,141 B2* | 11/2007 | Kathrani et al. | 604/500 |
| 7,776,056 B2* | 8/2010 | Henderson et al. | 606/130 |
| 7,927,272 B2* | 4/2011 | Bayer et al. | 600/129 |
| 8,021,162 B2* | 9/2011 | Sui | 434/274 |
| 2001/0037064 A1* | 11/2001 | Shahidi | 600/429 |
| 2002/0077544 A1* | 6/2002 | Shahidi | 600/424 |
| 2002/0120188 A1* | 8/2002 | Brock et al. | 600/407 |
| 2004/0106916 A1* | 6/2004 | Quaid et al. | 606/1 |
| 2005/0192595 A1* | 9/2005 | Green et al. | 606/130 |
| 2006/0089626 A1* | 4/2006 | Vlegele et al. | 606/1 |
| 2007/0060924 A1* | 3/2007 | Choi | 606/93 |
| 2008/0033240 A1 | 2/2008 | Hoffman et al. | |
| 2008/0306490 A1* | 12/2008 | Lakin et al. | 606/130 |
| 2009/0099544 A1* | 4/2009 | Munrow et al. | 604/506 |
| 2010/0094312 A1* | 4/2010 | Ruiz Morales et al. | 606/130 |
| 2010/0198402 A1* | 8/2010 | Greer et al. | 700/247 |
| 2011/0046637 A1* | 2/2011 | Patel et al. | 606/130 |
| 2011/0152878 A1* | 6/2011 | Trusty et al. | 606/130 |
| 2011/0245844 A1* | 10/2011 | Jinno | 606/130 |
| 2011/0301419 A1* | 12/2011 | Craft et al. | 600/202 |
| 2011/0306986 A1* | 12/2011 | Lee et al. | 606/130 |
| 2012/0101508 A1* | 4/2012 | Wook Choi et al. | 606/130 |

* cited by examiner

MEDICAL ROBOT SYSTEM AND METHOD FOR CONTROLLING THE SAME

CROSS-REFERENCE TO RELATED APPLICATIONS

This application claims the priority benefit of Korean Patent Application No. 10-2011-0131935, filed on Dec. 9, 2011, in the Korean Intellectual Property Office, the disclosures of which are incorporated herein by reference.

BACKGROUND

1. Field

Example embodiments of the following disclosure relate to a medical robot system and a method for controlling the same. More specifically, example embodiments of the following disclosure relate to a medical robot system and a method for controlling the same to improve stability of robotic surgery.

2. Description of the Related Art

Robotic surgery is a surgery in which a robot capable of moving a surgical apparatus is controlled by a doctor. Due to various benefits, robotic surgery is widely utilized in a variety of medical fields including general surgery.

Generally, a medical robot system includes a robot and a console to control movement of the robot. A doctor moves the robot by operating an input unit provided in the console and thereby incising or suturing the surgical site of a patient.

However, disadvantageously, a serial link-type medical robot system of the related art does not secure patient incision safety. Specifically, when the doctor operates the robot using a console, the doctor does not know a level of force applied to a patient incision by the robot, and thus, the patient's safety during performance of surgery is reduced.

As such, the doctor does not know the force applied to the incision by the robot. For this reason, it is difficult for the doctor to control force in order to prevent the incision of the patient from being damaged. Accordingly, the incision of the patient may be readily damaged.

Therefore, there is a need for a system and method of robotic surgery, which ensures the safety of the patient during surgery.

SUMMARY

Therefore, it is one aspect of the present disclosure to provide a medical robot system and a method for controlling the same to improve stability of robotic surgery.

Additional aspects of the present disclosure will be set forth in part in the description which follows and, in part, will be obvious from the description, or may be learned by practice of the present disclosure.

In accordance with one aspect of the present disclosure, provided is a medical robot system including: a trocar inserted into an incision of a patient, to guide a surgical apparatus and transmit at least one of position information of the surgical apparatus and pressure information of the surgical apparatus; and a console to display a screen including at least one of the position information and the pressure information.

The screen may include: a ring-shaped first icon corresponding to a reference range, wherein the reference range means an acceptable range allowing the surgical apparatus to move in a state in which the surgical apparatus is inserted into the trocar; a dot-shaped second icon displayed in the first icon, the dot-shaped second icon showing the position information of the surgical apparatus within the reference range; and a rod-shaped third icon showing the pressure information of the surgical apparatus.

The console may output an alarm when the position of the surgical apparatus is out of the reference range.

The alarm mode may include at least one of warning call, warning light, warning message display and blinking of the second icon.

The console may output an alarm when the pressure applied by the surgical apparatus exceeds a predetermined reference pressure.

The alarm mode may include at least one of warning call, warning light, warning message display and blinking of the second icon.

The reference range may be determined according to the diameter of the trocar.

The reference pressure may be determined according to the material of the trocar.

The trocar may transmit at least one of position information of the surgical apparatus and pressure information of the surgical apparatus to the surgical robot controlled by the console, and the surgical robot controls operation of the robot arm to which the surgical apparatus is joined, when the position of the surgical apparatus is out of a reference range or the pressure applied by the surgical apparatus exceeds a reference pressure.

The trocar may include: a position sensing unit to sense a position of the surgical apparatus in the trocar; a pressure sensing unit to sense a pressure applied to the trocar by the surgical apparatus; a control unit to periodically produce a message including the sensed position and pressure; and a transmission unit to periodically transmit the produced message to the console.

In accordance with another aspect of the present disclosure, provided is a method for controlling a medical robot system including: transmitting at least one of position information of the surgical apparatus and pressure information of the surgical apparatus to a console using a trocar that is inserted into an incision of a patient and guides a surgical apparatus; and displaying a screen including at least one of the position information and the pressure information using the console.

The screen may include: a ring-shaped first icon corresponding to a reference range, wherein the reference range means an acceptable range allowing the surgical apparatus to move in a state in that the surgical apparatus is inserted into the trocar; a dot-shaped second icon displayed in the first icon, dot-shaped second icon showing the position information of the surgical apparatus within the reference range; and a rod-shaped third icon showing the pressure information of the surgical apparatus.

The method may further include: outputting an alarm when the position of the surgical apparatus is out of the reference range.

The alarm mode may include at least one of warning call, warning light, warning message display and blinking of the second icon.

The method may further include: outputting an alarm when the pressure applied by the surgical apparatus exceeds a predetermined reference pressure.

The alarm mode may include at least one of warning call, warning light, warning message display and blinking of the second icon.

The reference range may be determined according to the diameter of the trocar.

The reference pressure may be determined according to the material of the trocar.

The method may further include: transmitting at least one of position information of the surgical apparatus and pressure information of the surgical apparatus to the surgical robot controlled by the console using the trocar; and controlling operation of the robot arm, to which the surgical apparatus is joined, using the surgical robot, when the position of the surgical apparatus is out of a reference range or the pressure applied by the surgical apparatus exceeds a reference pressure.

The transmitting may include: sensing a position of the surgical apparatus in the trocar using a position sensing unit; sensing a pressure applied to the trocar by the surgical apparatus using a pressure sensing unit; periodically producing a message including the sensed position and pressure; and periodically transmitting the produced message to the console.

BRIEF DESCRIPTION OF THE DRAWINGS

These and/or other aspects of the present disclosure will become apparent and more readily appreciated from the following description of the embodiments, taken in conjunction with the accompanying drawings of which.

DETAILED DESCRIPTION

Figure 1:
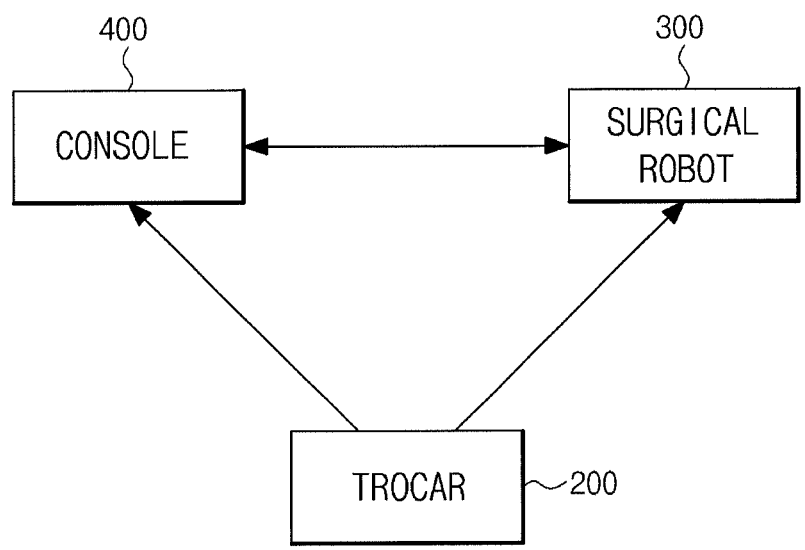
FIG. 1 illustrates a configuration of a medical robot system, according to an example embodiment of the present disclosure.

The advantages, features and their achieving methods of the present disclosure will be more clearly understood from the following detailed description taken in conjunction with the accompanying drawings. However, the embodiments disclosed in the following description are not limited thereto and are implemented in various forms. The present embodiments are provided only to realize complete disclosure of the present disclosure and to completely inform of those having a common knowledge in the related art the scope of the present disclosure and are not to be construed as limiting the scope of the disclosure.

Hereinafter, medical robot system and a method for controlling the same according to embodiments of the present disclosure will be described with reference to the accompanying drawings. Throughout the drawings, the same elements are denoted by the same reference numerals.

FIG. 1 illustrates a configuration of a medical robot system, according to an example embodiment of the present disclosure. As shown in FIG. 1, the medical robot system may include a console 400, a surgical robot 300, and a trocar 200.

The console 400 may transmit a control signal to the surgical robot 300 or receive image data from the surgical robot 300. In addition, the console 400 receives a message from the trocar 200. For this purpose, the console 400 may be connected to the surgical robot 300 or the trocar 200 via a network. In this case, the network may be a wired network or wireless network, or a combination thereof. The console 400 may display an image of a surgical site on the patient's body or information sensed by the trocar 200. A doctor may remotely control operations of the surgical robot 300 using the console 400. A more detailed description of the console 400 will be given below with reference to FIG. 5.

The surgical robot 300 receives a control signal from the console 400 via the network and moves according to the received control signal. The surgical robot 300 takes an image of a surgical site on a patient and transmits the image data of the image to the console 400 via the network. Further, the surgical robot 300 receives the message 100 transmitted from the trocar 200. A more detailed description of the surgical robot 300 will be given below with reference to FIG. 4.

The trocar 200 may be an apparatus that is inserted into an incision site of a patient and guides a surgical apparatus provided in the surgical robot 300. A body (not shown) of the trocar 200 may have a cylindrical shape and a through hole (not shown) through which the surgical apparatus is inserted, and may be provided in the center of the body. However, the present disclosure is not limited thereto. The trocar 200 is an apparatus inserted into the incision site of the patient and may be thus made of an elastic material to minimize damage to the incision. However, the material for the trocar 200 is not limited to the elastic material, and thus, other materials may be used.

In addition, the trocar 200 senses a position of the surgical apparatus when the surgical apparatus is inserted into the through hole of the trocar 200. Also, the trocar 200 senses a pressure applied to the trocar 200 by the surgical apparatus. A more detailed description of the trocar 200 will be given below with reference to FIG. 2.

Figure 2:
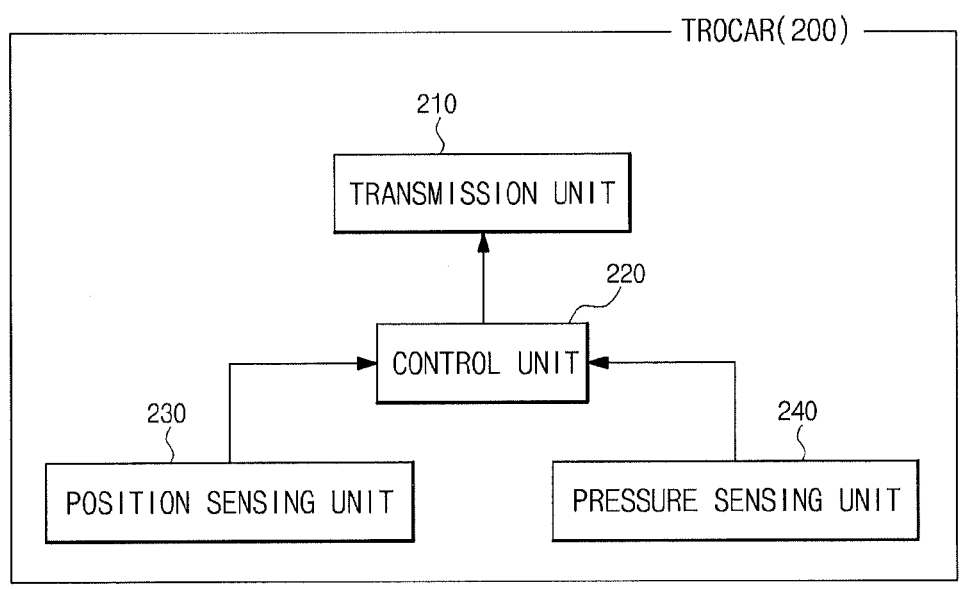
FIG. 2 illustrates a configuration of a trocar, according to an example embodiment of the present disclosure.

FIG. 2 illustrates a configuration of a trocar, according to an example embodiment of the present disclosure. As shown in FIG. 2, the trocar 200 may include a position sensing unit 230, a pressure sensing unit 240, a control unit 220, and a transmission unit 210.

The position sensing unit 230 may sense a position of the surgical apparatus in the through hole of the trocar 200. For this purpose, the position sensing unit 230 may include a position sensor. The position sensor is, for example, a photodiode array, however, the present disclosure is not limited thereto. As such, the photodiode array may be provided in the through hole of the trocar 200. The position information of the surgical apparatus sensed by the position sensing unit 230 may be supplied to the control unit 220 described in the following.

The pressure sensing unit 240 may sense the pressure applied to the trocar 200 through or by the surgical apparatus inserted into the through hole. For this purpose, the pressure sensing unit 240 may include a pressure sensor. The pressure sensor is, for example, a load cell, however, the present disclosure is not limited thereto. The load cell is a device to measure force or load. The pressure sensing unit 240 may be provided in the body of the trocar 200. For example, the pressure sensing unit 240 may be provided along the periphery of the through hole. The pressure information sensed by the pressure sensing unit 240 may be supplied to the control unit 220 described in the following.

The control unit 220 may produce a message 100 including position information supplied from the position sensing unit 230 and pressure information supplied from the pressure sensing unit 240. A more detailed description of the message 100 will be given below with reference to FIG. 3.

Figure 3:
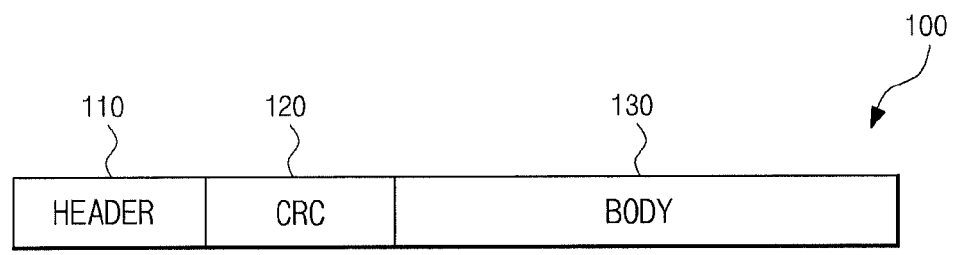
FIG. 3 illustrates a format of a message produced in the trocar of FIG. 2.

FIG. 3 illustrates a format of the message 100, according to an example embodiment of the present disclosure. As shown in FIG. 3, the message 100 includes a header field 110, a CRC field 120, and a body field 130.

The header field 110 is a field in which various information associated with the message 100 is recorded. For example, information such as the length of message, lengths of respective fields and an identifier to identify a start position of each region in the total message may be recorded.

The CRC field 120 is a field in which codes for cyclic redundancy check (CRC) may be recorded. The CRC codes may be used for identification of errors in the corresponding message 100 in an apparatus that receives the message 100. That is, in the process of receiving the message 100 via the network, the message 100 may be partially damaged or lost due to communication environments, and thus, errors may exist in the received message. In this case, the apparatus receiving the message 100 confirms CRC codes recorded in the CRC field of the message and thereby confirms generation of errors in the corresponding message 100.

The body field 130 is a field in which position information supplied from the position sensing unit 230 and pressure information supplied from the pressure sensing unit 240 are recorded.

Referring to FIG. 2 again, the control unit 220 periodically produces the message 100 of the format as shown in FIG. 3. For example, the message 100 may be produced in seconds. The message 100 produced in the control unit 220 may be supplied to the transmission unit 210.

The transmission unit 210 may transmit the message 100 supplied from the control unit 220 to the console 400 and/or the surgical robot 300. For this purpose, the transmission unit 210 may communicate with a communication unit (represented by reference numeral "430" in FIG. 5) of the console 400 and a reception unit (represented by reference numeral "310" in FIG. 4) of the surgical robot 300 in a wired or wireless manner.

Figure 4:
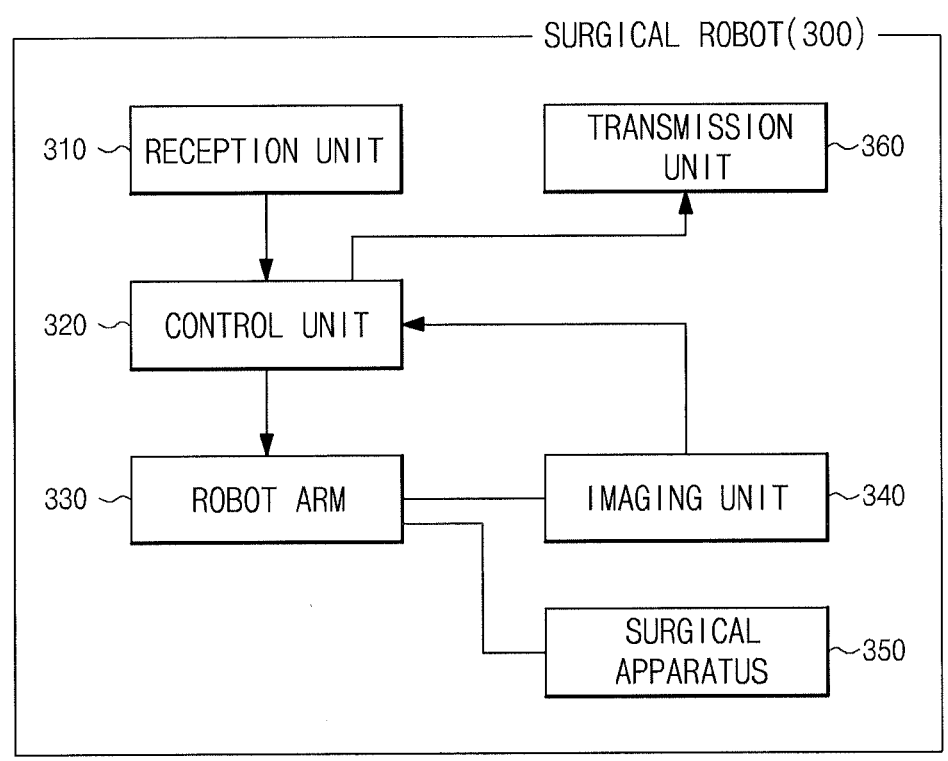
FIG. 4 illustrates a configuration of a surgical robot, according to an example embodiment of the present disclosure.

FIG. 4 illustrates a surgical robot 300, according to an example embodiment of the present disclosure. As shown in FIG. 4, the surgical robot 300 may include a reception unit 310, a transmission unit 360, a control unit 320, a robot arm 330, an imaging unit 340, and a surgical apparatus 350.

The reception unit 310 may receive a control signal from the console 400 and a message 100 transmitted from the trocar 200. The received control signal and the message 100 may be supplied to the control unit 320.

The control unit 320 may control the movement of the robot arm 330, according to the control signal received by the reception unit 310. Additionally, the control unit 320 analyzes the message 100 and limits operation of the robot arm 330, according to the analysis result.

Specifically, the control unit 320 analyzes the message 100 and thereby obtains position information of the surgical apparatus 350 and pressure information from the surgical apparatus 350. Then, the control unit 320 determines whether the present position of the surgical apparatus 350 is out of a reference range and whether a pressure applied to the trocar 200 by the surgical apparatus 350 is out of a reference range. Here, the reference range refers to an acceptable range, enabling the surgical apparatus 350 to move in a state that the surgical apparatus 350 is inserted into the through hole of the trocar 200. That is, the reference range refers to a range within which the surgical apparatus 350 does not damage an incision of a patient although the surgical apparatus 350 moves in a state in which it is inserted into the through hole of the trocar 200. As such, the reference range of the position and the reference range of the pressure increase the safety of the patient and reduce the possibility of damage to the incision of the patient.

As a result of the determination, when the position of the surgical apparatus 350 is out of the reference range, or the pressure applied to the trocar 200 by the surgical apparatus 350 is out of the reference range, the control unit 320 may be in an emergency state, that is, a state in which an incision of a patient is damaged by the surgical apparatus 350. As a result, the control unit 320 controls movement of the robot arm 330. When an emergency state occurs, the control unit 320 controls operation of the robot arm 330 according to the analysis result of the message 100, and when an emergency does not occur, the control unit 320 controls the operation of the robot arm 330, according to the control signal of the console 400.

Information required for determination of an emergency state occurrence, such as reference range or reference pressure may be stored in the memory unit (not shown) of the surgical robot 300, or may be stored in the memory unit after being received from the console 400.

The reference range may be set at a level that is the same as or smaller than the diameter of the through hole formed in the trocar 200. In addition, the diameter of the trocar 200 used for patients may be varied according to the type of surgery. A doctor may preset the reference range according to the diameter of the trocar 200. In this case, the doctor may set a reference range using the console 400, for example, however, the present disclosure is not limited thereto.

Unlike the reference range, the reference pressure may be stored in the process of producing a medical robot system. For example, the value of the reference pressure stored in the medical robot system is one. In this case, a doctor does not need to additionally set a reference pressure prior to operation. In another example, reference pressure stored in the medical robot system may be plural values. Specifically, a plurality of reference pressures is stored according to the material for the trocar 200 and the doctor selects the reference pressures according to the material of the trocar 200 used for operation.

The robot arm 330 is controlled by the control unit 320, which is provided at one end thereof with an imaging unit 340 and a surgical apparatus 350.

The imaging unit 340 may image a surgical site of a patient. The image obtained by the imaging unit 340 is supplied to the control unit 320 and is then subjected to image processing. Examples of image processing include enlargement, reduction, movement, rotation, editing and filtering of the obtained image. Dependent on embodiments, the image processing process performed by the control unit 320 may be omitted, if desired.

The surgical apparatus 350 is provided on the end of the robot arm 330 and is detachably designed on the robot arm 330. The operating surgeon moves the surgical apparatus 350 through an input unit provided in the console 400 and thereby incises or sutures the surgical site of the patient.

The transmission unit 360 may transmit the image processed by the control unit 320 to the console 400.

Figure 5:
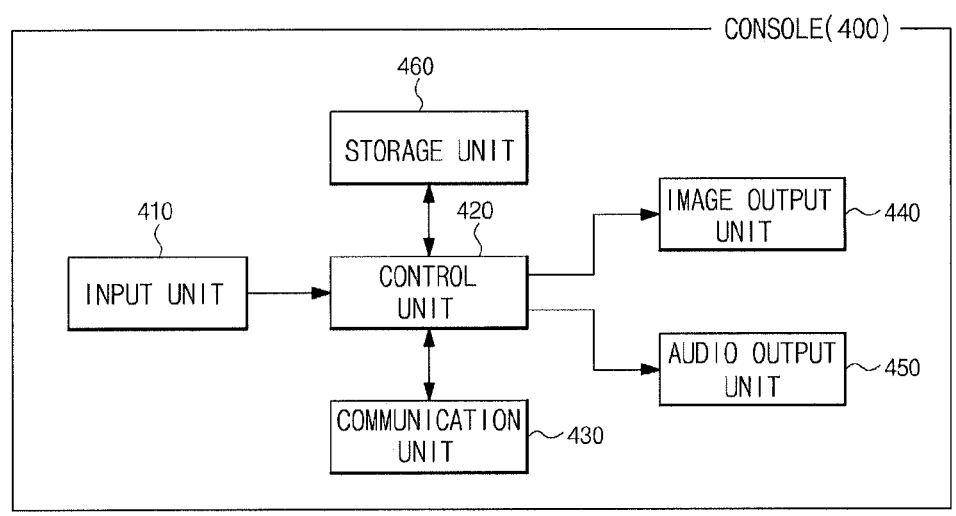
FIG. 5 illustrates a configuration of a console, according to an example embodiment of the present disclosure.

FIG. 5 illustrates a configuration of the console 400, according to an example embodiment of the present disclosure. As shown in FIG. 5, the console 400 may include an input unit 410, a storage unit 460, a control unit 420, a communication unit 430, an image output unit 440, and an audio output unit 450.

The input unit 410 receives instructions to control movement of the surgical robot 300 from a doctor. In addition, the input unit 410 receives information associated with the reference range from a user. Further, the user may set display of position information of the surgical apparatus, display of pressure information, alarm output upon the occurrence of an emergency state, and the like, through the input unit 410. For this purpose, the input unit 410 may include a plurality of buttons, keys, joysticks, and the like, however, the present disclosure is not limited thereto.

The storage unit 460 may store an algorithm or data required for controlling operations of the surgical robot 300. Further, the storage unit 460 may store data required for determination of occurrence of an emergency state, for example, information associated with the reference range and reference pressure. Moreover, the storage unit 460 may store predetermined information set by a user. Examples of the predetermined information include position information display of the surgical apparatus, pressure information display of the surgical apparatus, emergency alarm, alarm mode and the like. Examples of the alarm mode may include a warning call, a warning light, a warning message display, blinking of icons, and the like.

The storage unit 460 may be implemented by a nonvolatile memory device, such as, a read only memory (ROM), random access memory (RAM), programmable read only memory (PROM), erasable programmable read only memory (EPROM) and a flash memory, or a volatile memory device such as random access memory (RAM), or storage medium, such as, hard disk and optical disk. However, the storage unit 460 is not limited to these examples or may be implemented by any other forms known in the related art.

The communication unit 430 functions to transmit and receive data or a control signal between the console 400 and/or the surgical robot 300. Specifically, the communication unit 430 transmits the control signal to control operations of the surgical robot 300 to the surgical robot 300 and receives image data obtained by the imaging unit 340 of the surgical robot 300, depending on embodiments.

In addition, the communication unit 430 receives the message 100 transmitted from the trocar 200. The received message 100 may be supplied to the control unit 420.

The control unit 420 produces a control signal to control the surgical robot 300 according to the instruction input through the input unit 410 by the doctor. The control signal produced in the control unit 420 may be transmitted through the communication unit 430 to the surgical robot 300.

Further, the control unit 420 analyzes the message 100 received from the trocar 200 and thereby obtains position information of the surgical apparatus and pressure information of the surgical apparatus. Additionally, the control unit 420 constitutes an image including the obtained position information and pressure information. Depending on embodiments, the control unit 420 may constitute a screen (see reference numeral "500" in FIG. 6) in which position information of the surgical apparatus and pressure information of the surgical apparatus overlap an image received from the surgical robot 300. The image received from the surgical robot 300 may correspond to an incision site of the patient. In this case, the control unit 420 may constitute the screen with reference to the predetermined information stored in the storage unit 460. For example, as a result of referring to predetermined information, when only the pressure information of the surgical apparatus is set to be displayed, the control unit 420 constitutes a screen in which pressure information of the surgical apparatus overlaps an image received from the surgical robot 300. As a result of referring to the predetermined information, when both position information of the surgical apparatus and pressure information of the surgical apparatus are set to be displayed, as shown in FIG. 6, the control unit 420 constitutes a screen in which position information and pressure information of surgical apparatus overlap the image received from the surgical robot 300.

Figure 6:
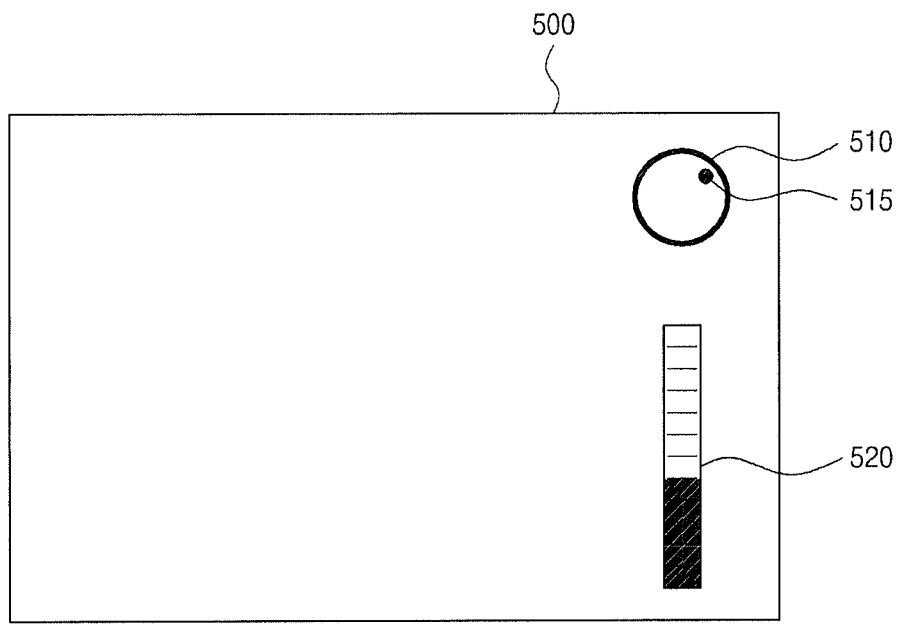
FIG. 6 illustrates a screen displayed in the console shown in FIG. 5.

Referring to FIG. 6, a ring-shaped first icon 510 corresponding to a reference range of the position may be displayed in the right upper part of the screen 500. Further, a dot-shaped second icon 515 may be displayed representing the present position of the surgical apparatus within the reference range in the first icon 510. In this case, the position at which the second icon 515 is displayed may be periodically updated. Specifically, the trocar 200 periodically transmits the message 100 which includes at least position information and the console 400 analyzes the message 100 and updates the position of the second icon 515 whenever it receives the message 100 from the trocar 200. A doctor can continuously confirm position of the surgical apparatus during surgery, since the position of the surgical apparatus in the trocar 200 is displayed on the screen. Further, when the position of the second icon 515 reaches a boundary of the first icon 510, the doctor performs surgery by suitably controlling the input unit 410 such that the incision is not damaged.

In addition, a rod-shaped third icon 520 showing pressure information may be displayed in the right lower part of the screen. FIG. 6 shows a case in which the third icon 520 is longitudinally long. In this case, the inside of the rod may be divided into a plurality of regions. When there is no pressure information on the surgical apparatus, each region of the inside of the rod may be displayed transparently, e.g., each region may be empty. When there is pressure information of the surgical apparatus, the rod turns in color from the bottom to the top of the rod in proportion to the pressure applied by the surgical apparatus. At this time, respective regions may be displayed in different colors. For example, green, yellow, orange and red may be displayed from the bottom to the top of the rod in this order. In another example, a region having a lower pressure than the reference pressure may be displayed in green, while a region having a higher pressure than the reference pressure is displayed in red.

The first icon 510, second icon 515, and third icon 520, and their respective shapes and positions are exemplary, and thus, the present disclosure is not limited thereto.

Referring to FIG. 5 again, the control unit 420 may determine whether the present position of the surgical apparatus is out of the reference range and whether the pressure applied to the trocar 200 by the surgical apparatus exceeds the reference pressure.

As a result of determination, when the position of the surgical apparatus is out of the reference range or the pressure applied to the trocar 200 by the surgical apparatus exceeds the reference pressure, the control unit 420 determines occurrence of an emergency state and outputs an alarm according to the alarm mode with reference to predetermined information stored in the storage unit 460. For example, when the alarm mode is set to blinking icon, the control unit 420 blinks at least one of the first icon 510 and the second icon 515 or blinks the third icon 520.

The image output unit 440 displays a screen constituted by the control unit 420. Specifically, the image output unit 440 displays the image obtained by the surgical robot 300, or a screen in which at least one of the position information and pressure information of the surgical apparatus overlaps the image obtained by the surgical robot 300. The image output unit 440 may be implemented by, for example, a liquid crystal display (LCD).

The audio output unit 450 audibly outputs an alarm associated with an emergency state. Such an audio output unit 450 includes, for example, a speaker, however, the present disclosure is not limited thereto.

Figure 7:
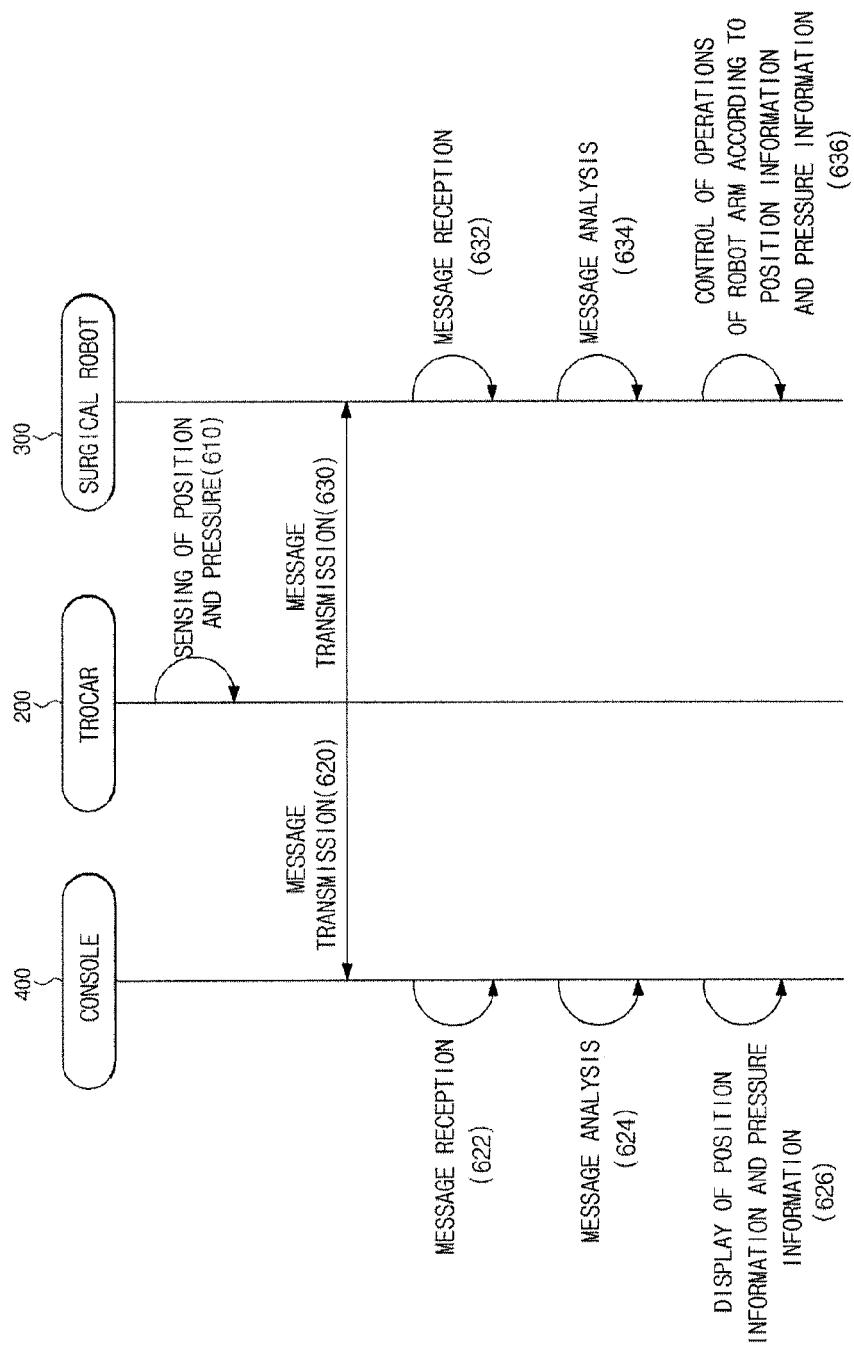
FIG. 7 is a flowchart illustrating a process for controlling a medical robot system, according to an example embodiment of the present disclosure.

FIG. 7 is a flowchart illustrating a process for controlling a medical robot system, according to an example embodiment of the present disclosure.

Prior to description, a state in which the trocar 200 is inserted into an incision of a patient is assumed. Under this state, a doctor inserts the surgical apparatus connected to the surgical robot 300 into the through hole of the trocar 200 by operating the input unit of the console 400, thereby inputting instructions to the input unit. Further, when the image obtained by the surgical robot 300 is transmitted to the console 400 and is displayed through the image output unit 440 of the console 400, the doctor performs surgery by operating the input unit 410 of the console 400 while monitoring the displayed image.

During surgery, the trocar 200 senses the position of the surgical apparatus in the through hole and the pressure applied to the trocar 200 by the surgical apparatus (610). At this time, sensing of the position and pressure of the surgical apparatus may be carried out by the position sensing unit 230 and the pressure sensing unit 240 of the trocar 200, for example.

When the position of the surgical apparatus and the pressure of the surgical apparatus are sensed, the trocar 200 produces a message 100 including position information and pressure information of the surgical apparatus and transmits the produced message 100 to the console 400 and the surgical robot 300 (620, 630), respectively.

The console 400 and the surgical robot 300 each receives the message transmitted from the trocar 200 (622, 632) and analyzes the received message 100 (624, 634). As a result, position information and pressure information of the surgical apparatus can be obtained from the received message 100.

When position information and pressure information of the surgical apparatus are obtained from the message 100, the surgical robot 300 controls operation of the robot arm 330 according to the obtained position information and pressure information (636) and the console 400 displays the obtained position information and pressure information (626). Specifically, a screen including position information and pressure information of the surgical apparatus is constituted and is displayed through the image output unit 440 of the console 400.

Specifically, as shown in FIG. 6, a first icon 510 corresponding to the referenced range is displayed in the right upper part of the screen 500 and a dot-shaped second icon 515 showing the present position of the surgical apparatus within the reference range is displayed in the first icon 510. In addition, a rod-shaped third icon 520 showing pressure information of the surgical apparatus is displayed in the right lower part of the screen 500.

Then, as a result of analysis of the newly received message 100, when the position of the surgical apparatus is out of the reference range, or the pressure applied to the trocar 200 by the surgical apparatus exceeds the reference pressure, the console 400 outputs an alarm associated with an emergency state. At this time, the alarm output or alarm mode may be in accordance with the predetermined information.

In the aforementioned embodiments, the components constituting the console 400, the surgical robot 300 and the trocar 200 may be realized by a "module". Here, the term "module" means, but is not limited to, a software or hardware component, such as a field programmable gate array (FPGA) or application specific integrated circuit (ASIC), which performs certain tasks. A module may be configured to reside in the addressable storage medium and configured to execute on one or more processors.

Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules. In addition, the components and modules execute one or more CPUs in a device.

The embodiments of the present disclosure in addition to the aforementioned embodiments may be implemented by media including computer readable code/commands to control at least one processing element, for example, computer readable media. The media correspond to medium/media enabling storage and/or transmittance of the computer readable codes.

The computer readable codes may be recorded in media or transmitted via the Internet. The results produced can be displayed on a display of the computing hardware. Examples of the media include recording media such as magnetic storage media (for example, ROM, floppy disc, hard disk or the like) and optical recording media (for example, CD-ROM or DVD) and transmission media such as carrier wave. Also, in embodiments of the present disclosure, the media may be signals such as composite signals or bitstreams. The media may be a distributed network and computer readable code may be stored/transmitted and executed in a distributed manner. Furthermore, in one example, the processing element includes a processor or a computer processor and the processing element may be dispersed and/or included in one device. Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Further, according to an aspect of the embodiments, any combinations of the described features, functions and/or operations can be provided.

Moreover, the medical robot system may include at least one processor to execute at least one of the above-described units and methods.

The medical robot system and a method for controlling the same according to the example embodiments of the present disclosure may have the following effects, described below.

A doctor may easily determine whether the present position of the surgical apparatus is out of a reference range, since the present position information of the surgical apparatus is displayed on a screen.

Further, the doctor easily determines whether the pressure applied to the trocar by the surgical apparatus is out of a reference range, since the pressure is displayed on the screen.

Further, an operating surgeon continuously monitors the present position information and pressure information of the surgical apparatus during surgery, thus preventing the surgical apparatus from damaging an incision.

Further, it is possible to prevent the surgical apparatus from damaging an incision and improve stability of robotic surgery, thereby increasing the safety of the patient undergoing the surgery.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A medical robot system, comprising:
   a trocar, inserted into an incision, configured to guide a surgical apparatus and transmit at least one of position information of the surgical apparatus and pressure information of the surgical apparatus such that a movement of the surgical apparatus is controlled based on the at least one of position information and pressure information; and
   a console configured to display a screen including a representation of at least one of the position information and the pressure information,
   wherein the screen includes,
      a first icon corresponding to a reference range, wherein the reference range indicates a range allowing the surgical apparatus to move in a state in which the surgical apparatus is inserted into the trocar,
      a second icon displayed in the first icon, the second icon representing the position information of the surgical apparatus within the reference range, and
      a third icon representing the pressure information of the surgical apparatus.

2. The medical robot system according to claim 1, wherein the console is configured to output an alarm according to an alarm mode when the position information indicates that a position of the surgical apparatus is out of the reference range.

3. The medical robot system according to claim 2, wherein the alarm mode comprises at least one of a warning call, a warning light, a warning message display, and blinking of the second icon.

4. The medical robot system according to claim 1, wherein the console is configured to output an alarm according to an alarm mode when the pressure information indicates that a pressure applied by the surgical apparatus exceeds a reference pressure.

5. The medical robot system according to claim 4, wherein the alarm mode comprises at least one of a warning call, a warning light, a warning message display, and blinking of the second icon.

6. The medical robot system according to claim 1, wherein the reference range is determined according to a diameter of the trocar.

7. The medical robot system according to claim 1, wherein a reference pressure is determined according to a material of the trocar.

8. The medical robot system according to claim 1, wherein the trocar is configured to transmit at least one of position information of the surgical apparatus and pressure information of the surgical apparatus to a surgical robot controlled by the console, and
   the surgical robot is configured to control operation of a robot arm to which the surgical apparatus is joined, when a position of the surgical apparatus is out of a reference range or a pressure applied by the surgical apparatus exceeds a reference pressure.

9. The medical robot system according to claim 1, wherein the trocar comprises:
   a position sensing unit configured to sense a position of the surgical apparatus in the trocar;
   a pressure sensing unit configured to sense a pressure applied to the trocar by the surgical apparatus;
   a control unit configured to periodically produce a message including the sensed position and pressure; and
   a transmission unit configured to periodically transmit the produced message to the console.

10. A method for controlling a medical robot system comprising:
    transmitting at least one of position information of a surgical apparatus and pressure information of the surgical apparatus to a console using a trocar that is inserted into an incision and guides a surgical apparatus such that a movement of the surgical apparatus is controlled based on the at least one of position information and pressure information; and
    displaying a screen including a representation of the at least one of the position information and the pressure information using the console,
    wherein the screen includes,
       a first icon corresponding to a reference range, wherein the reference range indicates a range allowing the surgical apparatus to move in a state in that the surgical apparatus is inserted into the trocar,
       a second icon displayed in the first icon, the second icon representing the position information of the surgical apparatus within the reference range, and
       a third icon representing the pressure information of the surgical apparatus.

11. The method according to claim 10, further comprising:
    outputting an alarm according to an alarm mode when the position information indicates that a position of the surgical apparatus is out of the reference range.

12. The method according to claim 11, wherein the alarm mode comprises at least one of a warning call, a warning light, a warning message display, and blinking of the second icon.

13. The method according to claim 10, further comprising:
    outputting an alarm according to an alarm mode when the pressure information indicates that a pressure applied by the surgical apparatus exceeds a predetermined reference pressure.

14. The method according to claim 13, wherein the alarm mode comprises at least one of a warning call, a warning light, a warning message display, and blinking of the second icon.

15. The method according to claim 10, wherein the reference range is determined according to a diameter of the trocar.

16. The method according to claim 10, wherein a reference pressure is determined according to a material of the trocar.

17. The method according to claim 10, further comprising:
    transmitting at least one of position information of the surgical apparatus and pressure information of the surgical apparatus to a surgical robot controlled by the console using the trocar; and
    controlling an operation of a robot arm, to which the surgical apparatus is joined, using the surgical robot, when a position of the surgical apparatus is out of a reference range or a pressure applied by the surgical apparatus exceeds a reference pressure.

18. The method according to claim 10, wherein the transmitting comprises:
    sensing a position of the surgical apparatus in the trocar using a position sensing unit;
    sensing a pressure applied to the trocar by the surgical apparatus using a pressure sensing unit;
    periodically producing a message including the sensed position and pressure; and
    periodically transmitting the produced message to the console.

* * * * *